United States Patent
Radwanski et al.

(10) Patent No.: US 11,000,551 B2
(45) Date of Patent: May 11, 2021

(54) RED BLOOD CELL PRODUCTS AND THE STORAGE OF RED BLOOD CELLS IN CONTAINERS FREE OF PHTHALATE PLASTICIZER

(71) Applicant: Fenwal, Inc., Lake Zurich, IL (US)

(72) Inventors: Katherine Radwanski, Highland Park, IL (US); Craig L. Sandford, Buffalo Grove, IL (US); Kyungyoon Min, Kildeer, IL (US); Bryan Blickhan, Libertyville, IL (US); Daniel Lynn, Spring Grove, IL (US); Tat Mui, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 62 days.

(21) Appl. No.: 15/974,914

(22) Filed: May 9, 2018

(65) Prior Publication Data

US 2018/0256721 A1   Sep. 13, 2018

Related U.S. Application Data

(62) Division of application No. 14/122,847, filed as application No. PCT/US2012/056100 on Sep. 19, 2012, now Pat. No. 9,993,389.

(60) Provisional application No. 61/536,370, filed on Sep. 19, 2011, provisional application No. 61/549,562, filed on Oct. 20, 2011, provisional application No. 61/566,409, filed on Dec. 2, 2011, provisional application No. 61/595,891, filed on Feb. 7, 2012.

(51) Int. Cl.
| | | |
|---|---|---|
| A61K 35/18 | (2015.01) | |
| A61K 45/06 | (2006.01) | |
| A01N 1/02 | (2006.01) | |
| A61J 1/10 | (2006.01) | |
| B32B 27/08 | (2006.01) | |
| B32B 27/30 | (2006.01) | |
| B32B 27/32 | (2006.01) | |
| A61J 1/14 | (2006.01) | |

(52) U.S. Cl.
CPC ............ *A61K 35/18* (2013.01); *A01N 1/0226* (2013.01); *A01N 1/0263* (2013.01); *A01N 1/0273* (2013.01); *A61J 1/10* (2013.01); *A61J 1/1468* (2015.05); *A61K 45/06* (2013.01); *B32B 27/08* (2013.01); *B32B 27/304* (2013.01); *B32B 27/32* (2013.01); *B32B 2270/00* (2013.01); *B32B 2307/7244* (2013.01); *B32B 2439/80* (2013.01)

(58) Field of Classification Search
CPC .. A61J 1/10; A61J 1/1468; C08K 5/11; C08K 5/1545; A01N 1/0263; A01N 1/0226; B32B 27/08; B32B 27/22; B32B 27/32; B32B 2270/00; B32B 2307/7244; B32B 2439/80; B32B 27/304; A61K 35/18; A61K 45/06

See application file for complete search history.

(56) References Cited

U.S. PATENT DOCUMENTS

| | | | |
|---|---|---|---|
| 4,140,162 A | 2/1979 | Gajewski et al. | |
| 4,286,597 A | 9/1981 | Gajewski et al. | |
| 4,505,708 A | 3/1985 | Gajewski et al. | |
| 4,670,013 A | 6/1987 | Barnes et al. | |
| 4,789,700 A | 12/1988 | Hull et al. | |
| 4,943,287 A | 7/1990 | Carmen | |
| 5,026,347 A | 6/1991 | Patel | |
| 5,236,716 A | 8/1993 | Carmen et al. | |
| 5,382,526 A | 1/1995 | Gajewski et al. | |
| 5,713,694 A | 2/1998 | Monda et al. | |
| 5,721,024 A | 2/1998 | Carmen et al. | |
| 5,769,839 A | 6/1998 | Carmen et al. | |
| 5,772,960 A | 6/1998 | Ito et al. | |
| 5,824,216 A | 10/1998 | Joie et al. | |
| 5,849,843 A | 12/1998 | Laurin et al. | |
| 5,955,519 A | 9/1999 | Neri et al. | |
| 6,046,274 A | 4/2000 | Grandjean et al. | |
| 6,150,085 A | 11/2000 | Hess et al. | |
| 6,162,396 A | 12/2000 | Bitensky et al. | |
| 6,468,258 B1 * | 10/2002 | Shang .................. A61J 1/10 128/DIG. 24 | |
| 6,579,583 B2 | 6/2003 | Patel | |
| 6,675,560 B2 | 1/2004 | Gott et al. | |
| 7,208,545 B1 | 4/2007 | Branner et al. | |
| 7,276,621 B2 | 10/2007 | Cook et al. | |
| 7,297,738 B2 | 11/2007 | Gosse et al. | |
| 7,595,421 B2 | 9/2009 | Grass et al. | |

(Continued)

FOREIGN PATENT DOCUMENTS

| | | |
|---|---|---|
| DE | 4022700 | 1/1992 |
| EP | 0138147 | 4/1993 |

(Continued)

OTHER PUBLICATIONS

Radwanski et al., in Abstract Presentations from the AABB Annual Meeting and CTTXPO San Diego, CA, Oct. 22-25, 2011 published on Sep. 12, 2011 in Transfusion, vol. 51, s3, SP63, p. 66A. (Year: 2011).*

(Continued)

*Primary Examiner* — John Kim
(74) *Attorney, Agent, or Firm* — Cook Alex Ltd.

(57) ABSTRACT

Red blood cell products and compositions are disclosed. The product includes a container made from PVC or a non-PVC material that is substantially free of a phthalate plasticizer but otherwise includes one or more non-phthalate plasticizers or extractable agents. The product includes a RBC concentrate which has been combined with an additive solution for storing the RBCs.

15 Claims, 5 Drawing Sheets

(56) References Cited

U.S. PATENT DOCUMENTS

| | | |
|---|---|---|
| 7,629,413 B2 | 12/2009 | Goodwin et al. |
| 7,754,198 B2 | 7/2010 | Whitehead et al. |
| 7,786,201 B2 | 8/2010 | Grass et al. |
| 8,026,314 B2 | 9/2011 | Hansel et al. |
| 8,283,411 B2 | 10/2012 | Gosse et al. |
| 8,329,796 B2 | 12/2012 | Grass et al. |
| 8,372,912 B2 | 2/2013 | Olsen et al. |
| 8,568,846 B2 | 10/2013 | Dakka et al. |
| 8,669,311 B2 | 3/2014 | Colle et al. |
| 2003/0157150 A1 | 8/2003 | Lee et al. |
| 2007/0135562 A1 | 6/2007 | Freese et al. |
| 2008/0183004 A1 | 7/2008 | Shieh et al. |
| 2009/0239208 A1 | 9/2009 | Mayaudon |
| 2009/0277532 A1 | 11/2009 | Neas et al. |
| 2010/0042066 A1 | 2/2010 | Kuhlein et al. |
| 2010/0298477 A1 | 11/2010 | Godwin et al. |
| 2011/0028624 A1 | 2/2011 | Arendt et al. |
| 2011/0065860 A1 | 3/2011 | Hidalgo et al. |
| 2011/0097563 A1 | 4/2011 | Sandford et al. |
| 2011/0098390 A1 | 4/2011 | Dakka et al. |
| 2011/0117647 A1* | 5/2011 | Mayaudon ............... A01N 1/02 435/374 |
| 2011/0281987 A1 | 11/2011 | Godwin et al. |
| 2012/0022197 A2 | 1/2012 | Dakka et al. |
| 2012/0329036 A1 | 12/2012 | Hess et al. |
| 2013/0011824 A1 | 1/2013 | Chan et al. |
| 2013/0137789 A1 | 5/2013 | Olsen et al. |
| 2013/0171385 A1 | 7/2013 | Dakka et al. |
| 2013/0303640 A1 | 11/2013 | Song et al. |
| 2013/0310471 A1 | 11/2013 | Becker et al. |
| 2013/0310472 A1 | 11/2013 | Becker et al. |
| 2013/0310473 A1 | 11/2013 | Becker et al. |
| 2013/0317152 A1 | 11/2013 | Becker et al. |
| 2013/0317153 A1 | 11/2013 | Grass et al. |
| 2013/0331491 A1 | 12/2013 | Becker et al. |
| 2013/0338276 A1 | 12/2013 | Becker et al. |
| 2014/0016883 A1 | 1/2014 | Van Waeg et al. |
| 2014/0024754 A1 | 1/2014 | Becker et al. |
| 2014/0086892 A1 | 3/2014 | Min et al. |
| 2014/0162045 A1 | 6/2014 | Bourassa et al. |
| 2014/0276527 A1 | 9/2014 | Sandford et al. |
| 2014/0309345 A1 | 10/2014 | Frenkel et al. |
| 2014/0336319 A1 | 11/2014 | Kim et al. |
| 2018/0018353 A1 | 1/2018 | Morrison et al. |

FOREIGN PATENT DOCUMENTS

| | | |
|---|---|---|
| EP | 0778030 | 10/2001 |
| EP | 1432758 | 11/2008 |
| EP | 1309384 | 1/2011 |
| EP | 2114854 | 11/2012 |
| EP | 2089210 | 10/2013 |
| EP | 2665358 | 11/2013 |
| EP | 2666819 | 11/2013 |
| EP | 2777393 | 9/2014 |
| EP | 2810982 | 12/2014 |
| ER | 0829267 | 8/2001 |
| ER | 1864964 | 11/2010 |
| ER | 2599766 | 6/2013 |
| ER | 2220154 | 6/2014 |
| IN | 1407/CHE/2008 A * | 6/2010 |
| IN | 2006CH00254 | 2/2016 |
| JP | 2003-171288 | 6/2003 |
| JP | 2014-223182 | 12/2014 |
| WO | WO 1993/014810 | 8/1993 |
| WO | WO 96/14741 | 5/1996 |
| WO | WO 2011/004390 | 1/2011 |
| WO | WO 2011/110350 | 9/2011 |
| WO | WO 2012/094585 | 7/2012 |
| WO | WO 2012/113609 | 8/2012 |
| WO | WO 2013/025277 | 2/2013 |
| WO | WO 2013/100875 | 7/2013 |
| WO | WO 2013/123127 | 8/2013 |
| WO | WO 2014/028481 | 2/2014 |
| WO | WO 2014/031852 | 2/2014 |
| WO | WO 2014/076717 | 5/2014 |
| WO | WO 2014/093438 | 6/2014 |
| WO | WO 2014/185872 | 11/2014 |
| WO | WO 2014/195055 | 12/2014 |
| WO | WO 2014/195056 | 12/2014 |

OTHER PUBLICATIONS

International Preliminary Report on Patentability and Written Opinion dated Mar. 25, 2014 for International Application No. PCT/US2012/056100.

International Search Report dated Dec. 12, 2012 for International Application No. PCT/US2012/056100.

H.R. Hill et al: "The Effects of Polyvinyl Chloride and Polyolefin Blood Bags on Red Blood Cells . . . Solution", Vox Sanguinis, vol. 81, No. 3, Oct. 1, 2001, pp. 161-166.

C.J. Draper et al: "Biochemical and Structural Changes in RBCs Stored . . . Hexanol", Transfusion, vol. 42, No. 7, Jul. 1, 2002, pgs. 830-835, XP55045604, ISSN: 0041-1132, . . . 00138.

Database WPI, Week 200403, Thomson Scientific, London, GB; AN 2004-026123, XP002688187 & JP 2003-171288 A Terumo Corp. Jun. 17, 2003 Abstract.

Chembumukulam S.B. et al: "PVC Containers for Collection . . . Components", WPI/Thomson, vol. 2008, No. 17, Dec. 28, 2007, XP 002617312 . . . Indian Patent Appln. No. IN2006CH00254.

Davey, R.J., et al., Characteristics of white cell-reduced red cells stored in tri-(2-ethylhexyl)trimellitate plastic, Transfusion, Oct. 1994, vol. 34(10): pp. 895-898.

Bui et al., "Human Exposure, Hazard and Risk of Alternative Plasticizers to Phthalate Esters", Science of the Total Environment, Jan. 2016, pp. 451-467, vol. 541.

Opinion on the Safety of Medical Devices Containing DEHP-Plasticized PVC or Other Plasticizers on Neonates and Other Groups Possibly at Risk by SCENIHR dated Feb. 6, 2008.

Opposition filed in Application EP2791425 for "Red Blood Cell Products and the Storage of Red Blood Cells in Containers Free of Phtalate Plasticizers" dated Jul. 5, 2018.

BASF, HEXAMOLL* DINCH Safety Data Sheet, dated Nov. 13, 2007.

Akzo Nobel brochure for "LANKOMARK LZB320", dated Apr. 24, 2002.

\* cited by examiner

Fig. 1
Fig. 2
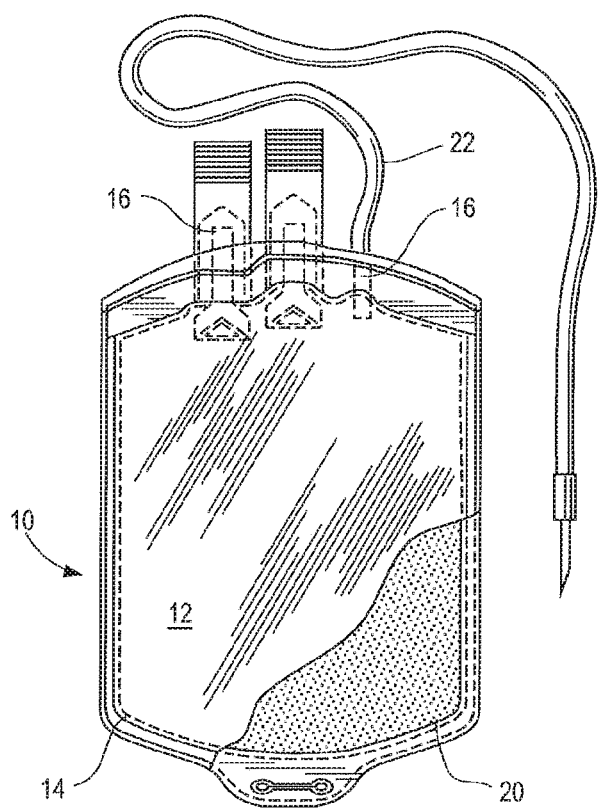
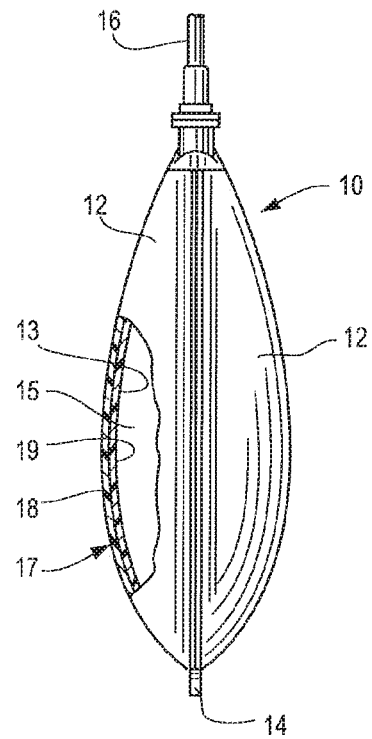

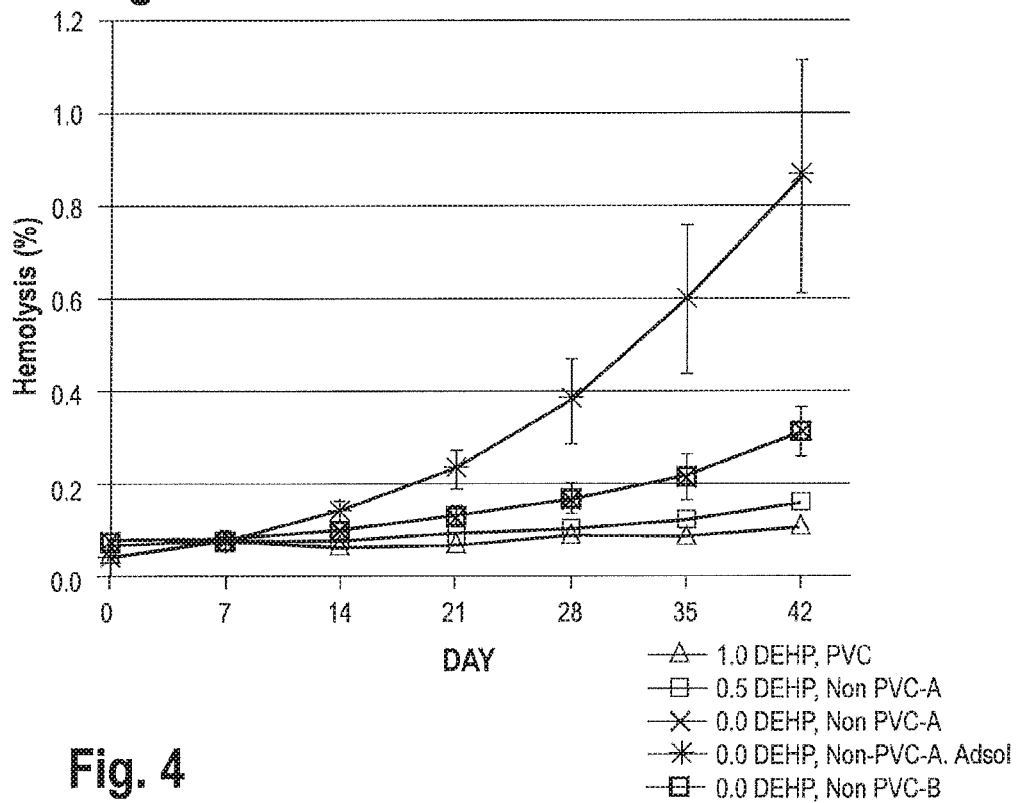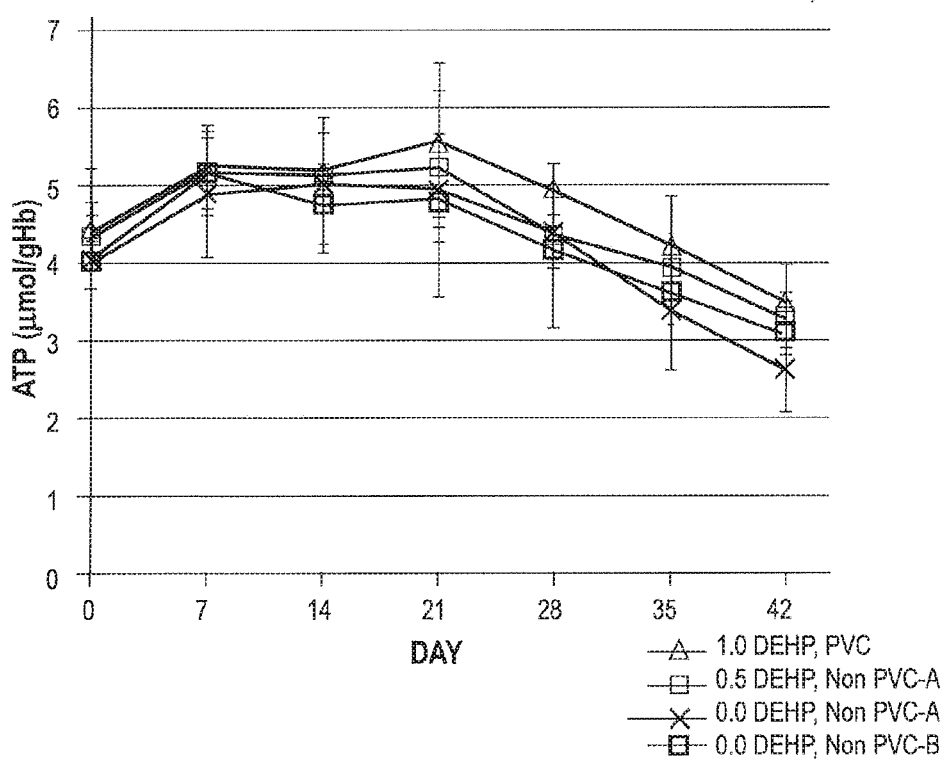

RED BLOOD CELL PRODUCTS AND THE STORAGE OF RED BLOOD CELLS IN CONTAINERS FREE OF PHTHALATE PLASTICIZER

CROSS-REFERENCE TO RELATED APPLICATIONS

This is a divisional application of U.S. patent application Ser. No. 14/122,847, now U.S. Pat. No. 9,993,389, filed Nov. 27, 2013 which is a U.S. National Stage of PCT Patent Application No. PCT/US12/56100, filed Sep. 19, 2012 which claims the benefit of U.S. Provisional Patent Application No. 61/536,370, filed Sep. 19, 2011, U.S. Provisional Patent Application No. 61/549,562, filed Oct. 20, 2011, U.S. Provisional Patent Application No. 61/566,409, filed Dec. 2, 2011, and U.S. Provisional Patent Application No. 61/595,891, filed Feb. 7, 2012, all of which are incorporated herein by reference in their entireties.

BACKGROUND

Red blood cells are often separated from whole blood and collected for later transfusion to a patient in need of red blood cells. For example, red blood cells (hereinafter "RBCs") may be administered to a patient suffering from a loss of blood due to trauma, as a post-chemotherapy treatment, or as part of a treatment of one or more blood borne diseases, such as certain anemias and the like. Unless administered immediately after collection from a donor, RBCs must typically be stored for some period of time prior to transfusion. The storage period may be anywhere from a few days to several weeks.

Prolonged storage of RBCs can (negatively) affect RBC function. In order for the RBCs to be suitable for transfusion to the recipient, RBCs must maintain adequate cell function and metabolism. For example, RBCs must maintain an adequate concentration of adenosine triphosphate (ATP) and 2,3-DPG. In addition, the presence of lactate must not be too high in the stored RBCs. Still further, stored RBCs must have acceptably low levels of hemolysis. Typically, an acceptable level of hemolysis is below 1.0% (in, for example, the U.S.) and 0.8% (in Europe) after 42 day storage.

Media for providing a storage environment for RBCs that will allow cell function and cell metabolism to be preserved and maintained have been developed and are commonly used. The media developed for RBCs can prolong the storage life of RBCs for up to 42 days. Such media (or "storage solutions") often include a nutrient for the RBCs, a buffer to help maintain the pH of the RBCs, electrolytes, a RBC membrane-protecting compound and other additives to enhance and extend the life of the RBCs. Examples of widely used and accepted storage media are Adsol and SAG-M, available from Fenwal, Inc., of Lake Zurich, Ill. Adsol and SAG-M include sodium chloride, glucose, mannitol, and adenine. Both Adsol and SAG-M have a pH of about 5.0 (referred to herein as "low pH") and are substantially isotonic.

Other additive solutions are disclosed in U.S. Patent Application Publication Nos. 2009/0239208 and 2011/0117647 both of which are incorporated by reference herein in their entireties. The additive solutions disclosed therein are, hypotonic, synthetic aqueous storage solutions for the prolonged storage of RBCs. The storage media disclosed therein typically include adenine, mannitol, sodium citrate, sodium phosphate, and glucose as the nutrient. These hypotonic aqueous additive solutions have a "high" pH of at least about 8.0.

During storage, concentrated RBCs and the additive solutions in which they are stored are typically kept in a sealed container, usually made of a plastic material. Most typically, the containers approved for the collection of whole blood and the storage of RBCs are made of a polyvinyl chloride (PVC). Inasmuch as polyvinyl chloride can be somewhat rigid or brittle, a plasticizer is typically incorporated into the PVC. Examples of currently known and used plasticizers for medical grade PVC are DEHP, TEHTM, and the family of citrate esters described in U.S. Pat. No. 5,026,347, the contents of which is also incorporated by reference herein.

As reported in U.S. Pat. No. 5,026,347 and other literature, such as Rock, et al. "Incorporation of plasticizer into red cells during storage," Transfusion, 1984; Horowitz et al. "Stabilization of RBCs by the Plasticizer, Di(ethylhexyl) phthalate," Vox Sarguinis, 1985, certain plasticizers may have a beneficial effect on the storage life of RBCs. More particularly, plasticizers such as DEHP and the family of citrate esters have been found to suppress hemolysis of RBCs stored in containers that include such leachable plasticizers. RBCs stored in containers made of plasticized PVC or a non-PVC container with plasticizer added (as described in U.S. Pat. No. 5,026,347) have traditionally been combined with an isotonic, low pH storage solution (such as Adsol). While DEHP plasticized containers have worked well for the storage of red cells, the use of other container materials and additive solutions to provide a suitable storage environment for red blood cells remains a topic of keen interest.

Thus, it would be desirable to provide a storage environment for RBCs wherein (1) the container is made of (a) a non-PVC material that is at least substantially free of any leachable phthalate plasticizer or (b) PVC material plasticized with a non-phthalate plasticizers and (2) a suitable storage media. As used herein, the term "storage environment" refers to the materials and solutions that contact the RBCs during storage.

SUMMARY

In one aspect, the present disclosure is directed to RBC products. The products include a container in which the wall of the container defines an interior chamber. At least a portion of the wall is made of a plastic combined with at least one non-phthalate plasticizer or other extractable agent. The product further includes a suspension of RBCs contained within the chamber. The suspension includes concentrated RBCs in a hypotonic solution. The hypotonic, chloride-free solution includes at least a nutrient, a buffer, and has a pH of greater than approximately 8.0. In a more specific aspect, the plastic may be PVC or a non-PVC composition.

In another aspect, the present disclosure is directed to a transfusible RBC composition. The composition includes a suspension of RBCs that includes concentrated RBCs substantially free of a phthalate plasticizer and having a hemolysis level of below at least 1.0% for its storage life.

In another aspect, the present disclosure is directed to a method for providing a transfusible red blood cell product. The method includes deriving red blood cell concentrate from whole blood, combining the concentrate with a hypotonic solution and storing the combination of concentrate and solution in a container that includes a polymeric material that is substantially free of phthalate.

In a further aspect, the present disclosure is directed to a container for storing red blood cell compositions. The container includes one or more container walls defining an interior chamber. The container wall(s) is made of a polymeric material that is free of phthalate and includes at least a first extractable agent and a second extractable agent wherein each of the at least first and second extractable agents is effective in suppressing hemolysis in red blood cells. In a more specific aspect, the polymeric material may include polyvinyl chloride (PVC) or may be a non-PVC material.

In another aspect, the present disclosure is directed to a red blood cell product that includes a container having one or more container wall(s) defining an interior chamber. The container wall is made of a polymeric material that is free of phthalate and includes at least a first and second extractable agent, each of which is effective in suppressing hemolysis in red blood cells. A suspension of red blood cells is contained within the interior chamber and includes concentrated red blood cells and an additive solution that includes a nutrient.

BRIEF DESCRIPTION OF THE DRAWINGS

FIG. 1 is a plan view of a typical RBC storage container used for storing the RBC suspension described herein;

FIG. 2 is a side view of the container of FIG. 1;

FIG. 3 is a graph comparing the levels of hemolysis in various containers having different amounts of a plasticizer (including no plasticizer);

FIG. 4 is a graph showing the levels of ATP over a 42-day storage period of RBCs stored in containers having varying levels of plasticizer (including no plasticizer);

DETAILED DESCRIPTION

Figure 5:
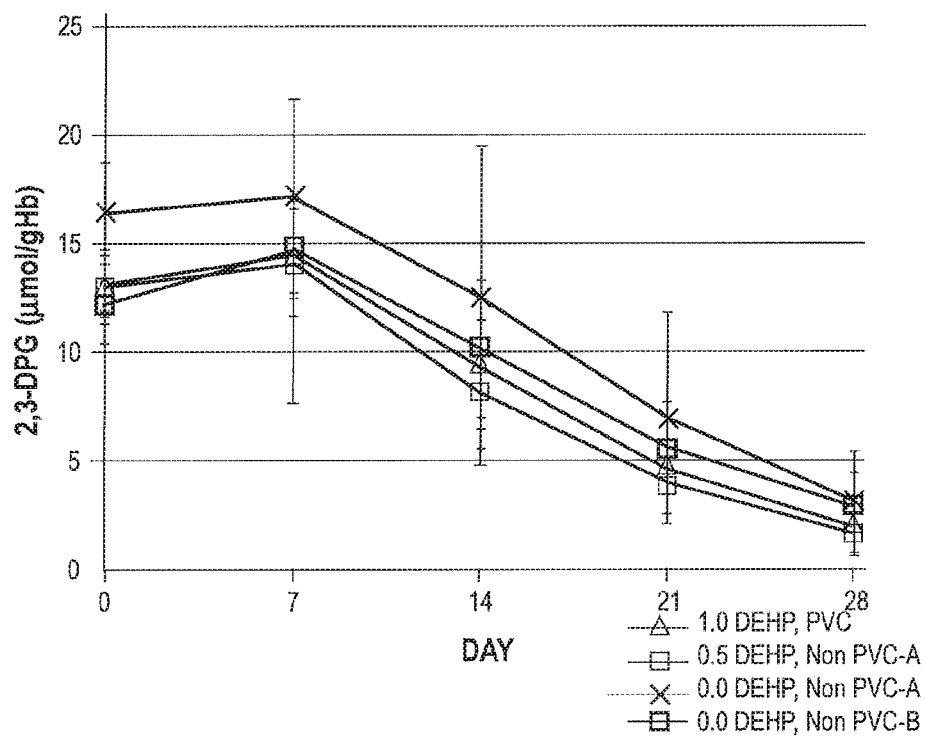
FIG. 5 is a graph showing the levels of 2,3-DPG over a 42-day storage period of RBCs stored in containers having varying levels of plasticizer (including no plasticizer)

Disclosed herein are RBC products that include (a) a RBC composition, and (b) a container for holding the composition during a period of storage. The RBC composition itself includes concentrated RBCs that have been combined with an additive solution selected to maintain cell function and metabolism of the RBCs during prolonged storage (e.g., at least about 42 days and possibly even up to at least 49 and/or 56 days). The container is typically made of a plastic material and more specifically a plastic material that does not include a phthalate plasticizer but may otherwise include one or more non-phthalate plasticizers or extractable agents. The RBCs of the RBC product are suitable for transfusion to a patient.

As noted above, RBC compositions include RBC concentrate and an additive solution. Concentrated RBCs are derived from whole blood either by manual or automated separation collection techniques which will be known to those skilled in the art. RBC concentrates may include some residual amount of plasma. In one embodiment, the RBC concentrate may have most of its plasma removed as described, for example, in International Application Publication WO/2011/049709, incorporated herein by reference.

Regardless of how much plasma remains with the RBCs, the additive solution is one that allows for the extended storage of RBCs (in the containers described herein) for over 21 days, over 35 days, up to at least 42 days, and even up to at least 49 and/or 56 days. In one embodiment, suitable additive solutions include at least sodium chloride, glucose (nutrient), mannitol and adenine. In a specific example, the additive solution includes approximately 111 mM glucose (dextrose), 154 mM sodium chloride, 41 mM mannitol and 2.0 mM adenine. The solutions may have a pH of about 5.0 and are substantially isotonic. Such solution is commonly known as Adsol and is available from Fenwal, Inc., of Lake Zurich, Ill. In another embodiment, additive solutions suitable for the storage of RBCs in accordance with the present disclosure are generally hypotonic and typically (but not necessarily) do not include sodium chloride. Such storage solutions also include a nutrient, a buffer, other additives such as sodium citrate, and typically have a pH of about 8.0 or higher. More specific examples of hypotonic, high pH additive solutions are described in U.S. Patent Publication Nos. US 2009/0239208 and US 2011/0117647, both of which are also incorporated herein by reference. In a specific embodiment, the additive solutions include between about 1 to 2.2 mM of adenine; about 20 mM to about 110 mM of mannitol; about 2.2 mM to about 40 mM sodium citrate; about 16 mM to about 30 mM sodium phosphate dibasic and about 20 mM to about 140 mM of glucose. The pH of the additive solution is above about 8.0.

In a more specific example, the additive solution useful in the storage of concentrated RBCs in accordance with the present disclosure includes about 2.0 mM of adenine; about 41 mM of mannitol; or about 25 mM of sodium citrate; about 20 mM of sodium phosphate dibasic and about 111 mM of glucose. The solution described above is referred to herein as "E-Sol 5."

Thus, concentrated RBCs with some or most of the plasma removed are combined with additive solutions of the type described above to provide the RBC composition. In one embodiment, the RBC composition includes between about 80 to 150 ml of the additive solution combined with about 180 to 250 ml of the concentrated RBCs. More preferably, the volume of additive solution may be about 100-110 ml.

In the collection of RBCs, it is typical to remove leukocytes from, or at least reduce the number of leukocytes in, the RBCs prior to their storage and transfusion. RBCs suspended in an additive solution are often subjected to a leuko-reduction step which commonly includes filtration of the RBC/additive solution.

In accordance with one embodiment of the methods and systems disclosed herein, RBCs are subjected to a filtration step or other treatment whereby one or both of leukocytes and prions are substantially removed (or the populations of leukocytes and/or prions are substantially reduced) from the RBCs. In such embodiment, concentrated RBCs may be combined with an additive solution of the type described above and the combined concentrated RBC/additive solution composition may be subjected to the leukocyte and/or prion removal (e.g., filtration) step.

In another embodiment, the RBC concentrate may be "leuko-reduced" and/or "prion-reduced" prior to combination with the additive solution. Thus, in this embodiment, RBC concentrate separated from whole blood is filtered by passing the RBC concentrate through a leuko-reduction filter. Alternatively, the whole blood may be subjected to leuko-reduction (i.e., leuko-filtration) and/or prion reduction/removal prior to separation of the RBCs from the whole blood. In any event, the RBCs are "leuko-reduced and/or "prion-reduced." Filters suitable for removing leukocytes (and/or prions) from whole blood or RBC concentrate (prior to the addition of the additive solution) include, but are not limited to, the Sepacell R-500 II, RZ-2000, RS-2000, Flex-Excel, Pure-RC, RZ-200 and R-3000. (Of course, other means for removing and/or reducing the number of leukocytes may also be used.) In this embodiment, the (now) leuko-reduced RBC concentrate is combined with the hypotonic additive solution of the type described above. The hypotonic additive solution may be added after introduction of the RBC concentrate into the container, or may already be present in the container at the time of RBC concentrate introduction.

Leuko-reduced (and/or prion-reduced) RBC concentrate (either with or without additive solution) is then introduced into a container which may be made of (a) a non-PVC material that is at least substantially free of phthalate plasticizer but preferably includes one or more non-phthalate plasticizer(s) or extractable agent(s), as described in greater detail below, (b) a container made of PVC that is at least substantially free of phthalate plasticizer but is plasticized with or otherwise includes one or more non-phthalate plasticizer(s) or extractable agent(s) (such as, but not limited to, the above-described DINCH plasticizer), also as described below or (c) any other container suitable for the long term storage of RBCs.

Containers for storing the RBC compositions disclosed herein may be permeable to oxygen or at least semipermeable to oxygen. As shown in FIGS. 1 and 2, container 10 may include one or more container walls 12 which define an interior chamber 15 for receiving the RBC composition 20. In one embodiment, two sheets made of a plastic material are brought together and sealed along their peripheries 14 to form container 10. Other ways of making container 10 will be known to those of skill in the art and are within the scope of the present disclosure. As shown in FIG. 2, container wall 12 includes an inner surface 13 which contacts the RBCs and an outer surface 17. In one embodiment, container wall may be made of a single layer of a polymer material, such as PVC or non-PVC polymer or polymer blend. In another embodiment, container wall 12 may be made of a multiple sheet laminate wherein inner surface 13 is made of one material and outer surface 17 is made of a different material. Container 10 may include one or more access ports 16 for connection with tubing 22, docking devices and the like to establish flow into and out from the interior chamber 15 of container 10.

In one embodiment, containers useful in the storage of RBCs as described above include container walls that are made in whole or at least in part of a plastic material that may include at least one or more polymeric compounds. The one or more plastic and/or polymeric compounds may be blended together and formed into flat sheets that are sealed together in the manner described above. The polymeric material may be made from or otherwise include polyvinyl chloride (PVC) or one or more non-PVC polyolefin homopolymers, copolymers or blends thereof. Examples of suitable non-PVC polyolefins include polypropylene, polyethylene, including ultra low density polyethylene (ULDPE) and very low density polyethylene (VLDPE). Other suitable compounds that may be used in the plastic materials of the containers or as part of the blend for making the plastic materials include ethylene vinyl acetate (EVA) and block copolymers such as Kraton®. Exemplary formulations and/or the polyolefins, polyolefin blends or other polymeric compounds which are useful, either alone or in combination, in the manufacture of containers suitable for use in the RBC products of the present disclosure are described in U.S. Pat. Nos. 5,026,347, 4,140,162, 5,849,843, and 6,579,583, all of which are incorporated herein by reference in their entireties.

As indicated above, the structure of the container or container wall may include one, two or more layers. The layer formulations may include one, two, three or more components. These structures should be suitable for sterilization by appropriate means, such as steam, ionizing radiation or ethylene oxide. Structures suitable for steam sterilization should resist distortions to high temperatures up to 121° C. This typically requires incorporation of materials with a melting peak of greater than 130° C. The preferred structure of autoclavable material suitable for the invention will incorporate polypropylene homopolymer or copolymer at a level of 30% or more in at least one of the layers to provide thermal resistance. A suitable polypropylene copolymer is supplied by Total Petrochemicals (random copolymer 6575). However, thermal resistance can also be obtained by crosslinking a lower melting material. For example, a 28% vinyl acetate EVA can be crosslinked by ionizing radiation sufficiently to withstand autoclave temperatures even though it has a melting point of 76° C. Suitable materials include Arkema Evatane® 28-03 and Celanese Ateva® 2803. The preferred structure is highly flexible, having a composite modulus of not more than 20,000 psi.

In some cases, it may be desirable for the structure to have radio frequency (RF) response to enable heat sealing. This can be accomplished by incorporating an RF responsive material such as described in U.S. Pat. No. 5,849,843.

Preferred structures for radiation sterilized applications will incorporate at least 30% of an ethylene based polymer (LDPE, LLDPE, ULDPE, VLDPE, EVA) in at least one of the layers. Structures of polypropylene copolymers and polypropylene polymers blended with elastomers such as Kraton® or ULDPE are also suitable for radiation sterilized applications. The preferred structure incorporates lower modulus components in at least one of the layers to enhance flexibility and toughness. These lower modulus components can be ultra low density polyethylene (ULDPE—typical density less than 0.90 Kg/L), very low density polyethylene (VLDPE—typically density less than 0.925 Kg/L), ethylene vinyl acetate copolymers (EVA) with greater than 16% vinyl acetate content, styrene butadiene terpolymers such as Kraton®. ULDPE materials are commercially available as Mitsui TAFMER®, Exxon Mobil Exact® and Dow Affinity®. EVA materials are available as Arkema Evatane® and Celanese Ateva®. These materials are incorporated at levels sufficient to obtain a composite modulus of less than 20,000 psi while maintaining resistance to distortion at temperatures greater than 121° C. for autoclaved applications. The disclosure of suitable non-PVC plastics set forth above is not meant to be exhaustive and it will be appreciated that other non-PVC plastics, polymers and blends thereof may also be used in the products and compositions of the present disclosure.

Containers of the type described herein may have a container sheet (wall) thickness of between approximately 0.010 to 0.018 inches. They may include a non-smooth or any surface finish that minimizes sheet sticking. Typically, containers of the type described herein may have a container volume (i.e., interior chamber volume) of approximately 150 ml to 4L.

As discussed above, containers useful in the methods, systems, and products disclosed herein may include PVC or be substantially free of PVC. Thus, one embodiment, the formulations used to make container walls 12 of container 10 are at least substantially free of polyvinylchloride (PVC). At the very least, surface 13 of container wall 12 is substantially free of PVC. In an embodiment where container 10 is made of a multiple sheet laminate the sheet providing inner surface 13 may be made substantially of a non-PVC material while the sheet providing outer surface 17 may be made of a different material. More typically, however, the container wall 12 may be made of a single sheet of a non-PVC polyolefin, as described above.

Of course, even in containers where the walls 12 are made without any PVC, some PVC may be present in small amounts. For example, ports 16 may include plasticized PVC. In any event, as used herein, the terms "substantially PVC-free" or "substantially free of PVC" refer to containers in which the walls that are in contact with the RBC composition, i.e., that part of the container that makes up a part of the storage environment, are made from a material that is free of PVC.

Containers suitable for use in the products, systems and methods of the present disclosure are at least substantially free of phthalate plasticizer, such as DEHP. This applies to containers where the polymeric material is PVC plastic as well as where the polymeric material is a non-PVC plastic. In the case of a container that includes PVC, such container material will have to be plasticized due to the brittle nature of PVC. As noted above, the plasticizer is a non-phthalate plasticizer. Non-phthalate plasticizers that may be suitable for use in the PVC containers described above include, for example, triethylhexyltrimellitate (TEHTM) and the family of citrate esters, as described in U.S. Pat. No. 5,026,347. Preferably, the PVC may be plasticized with 1,2-cyclohexane dicarboxylic acid diisononyl ester, known by its trade name, DINCH. In an embodiment where the polymer in the container material formulation is PVC, at least 10%, by weight, of the formulation is preferably one or more preferably hemolysis-suppressing, non-phthalate plasticizers such as DINCH or a citrate ester such as n-butyryltri-n-hexyl citrate. In an embodiment, PVC containers of the type described above may include approximately 55-80%, by weight, PVC resin and approximately 20-45%, by weight, of non-phthalate plasticizer(s) wherein a preferred plasticizer is DINCH, and less than about 3.0% of stabilizers and lubricants. In a more specific embodiment, containers of the type described above may include approximately 60-70% PVC resin, 20-35% DINCH plasticizer, approximately 4-10% epoxidized oil and approximately 0.5-3.0% additional co-stabilizers and lubricants. DINCH is available from, for example, BASF of Ludwigshafen, Germany.

In the case of non-PVC containers, such containers may likewise be free of phthalate plasticizers but include non-phthalate plasticizer. With respect to either the PVC or the non-PVC containers, at least a portion of the container wall, i.e., the portion or surface that is in contact with the RBCs during storage, is at least substantially free of phthalate plasticizer. For example, with reference to FIG. 2, at least inner surface 13 (or that portion of inner surface 13 that is in contact with the RBCs) may be substantially free of phthalate plasticizer. Thus, the storage environment in which the RBCs reside is at least substantially free of phthalate plasticizer. In a more specific embodiment, the storage environment in which the RBCs reside is at least substantially free of phthalate plasticizer, includes a non-phthalate plasticizer and further includes a suitable storage solution (such as those previously described).

Thus, for example, the PVC or non-PVC container (or more specifically, the container wall) is at least substantially free of a phthalate plasticizer but may include a non-phthalate plasticizer or extractable agent such as the citrate esters described in U.S. Pat. No. 5,026,347, or the DINCH plasticizer described above. Accordingly, such non-phthalate plasticizer(s) will be present in and part of the RBC storage environment. As the containers disclosed herein are often part of a larger processing set that includes tubing, ports, membranes and connectors in addition to being part of the storage environment, non-PVC and non-phthalate materials of the type described herein may also be used in the manufacture of such other processing set components.

In the embodiments described above, where the plastic container material may be PVC or a non-PVC composition, where no phthalate plasticizer or agent is included, and the material includes a single non-phthalate plasticizer (such as DINCH), a hypotonic, high pH storage media may preferably be used in the red blood cell composition, as demonstrated in Studies 4-6 below.

RBC compositions (which include RBC concentrates and hypotonic, high pH additive solutions) may be stored in the substantially phthalate-free containers. The RBC compositions stored in such containers may be stored for more than 21 days, more than 35 days and up to at least 42 days or even up to at least 49 days and/or 56 days, while maintaining acceptable storage cell function parameters (i.e., a level of ATP, 2,3-DPG, lactate). In particular, RBC compositions stored in the containers described above and that are substantially phthalate-free maintain hemolysis levels below 1.0% and even below 0.8% at, for example, 42 days of storage. Similarly, the RBC compositions stored for at least about 42 days also include ATP, 2,3-DPG, lactate, potassium, phosphate levels that are comparable to RBC compositions stored in plasticized PVC containers, as shown in the Studies reported herein.

In another embodiment, the plastic composition may include two or more plasticizers or extractable agents. The plastic container material may be either PVC or the non-PVC materials described above. Likewise, the structure of the container may also be as described above (single layer or multiple layers). Thus, in such an embodiment, the plastic composition may include a first extractable agent and a second extractable agent. At least one of the agents is preferably a non-phthalate extractable agent/plasticizer (e.g., not DEHP). In an embodiment where both the first and the second extractable agents/plasticizers are non-phthalate plasticizers, one of the agents/plasticizers may be a non-phthalate, extractable agent that can suppress hemolysis such as, but not limited to, the citrate ester n-butyryl-n-hexyl citrate (BTHC). More preferably, at least the first and second extractable agents or plasticizers are extractable agents or plasticizers, each effective in suppressing hemolysis in RBCs. Thus, in the embodiment where BTHC is one of such extractable hemolysis-suppressing agents, the other of the at least first or second agents or plasticizers may be a non-phthalate plasticizer, such as DINCH, which also is effective in suppressing hemolysis.

In another embodiment, the plastic composition may include a first and second extractable agent/plasticizer (wherein one of the first or second agents/plasticizers is preferably BTHC) and a further or third agent or plasticizer. The further or third agent/plasticizer may likewise be a non-phthalate agent/plasticizer. The third plasticizer may be a plasticizer that is not readily extractable or marginally extractable, such as TEHTM or epoxidized oil (which also acts as a stabilizer). Alternatively or in addition, the third (or further) plasticizer may be more readily extractable, such as the citrate ester acetyltri-n-butyl citrate (ATBC), which is also effective in suppressing hemolysis, or DINCH. Additional agents or plasticizers may further be included in the formulation of the containers described herein.

In a more specific embodiment, where the polymer in the container material formulation is PVC, at least 10%, by weight, of the formulation includes preferably two or more non-phthalate plasticizers wherein one of the plasticizers is DINCH or a citrate ester such as n-butyryltri-n-hexyl citrate (BTHC). In an embodiment, containers of the type described above may include approximately 55-80%, by weight, PVC resin and approximately 20-45%, by weight, of at least first and second phthalate plasticizer(s) wherein a preferred plasticizer is BTHC and/or DINCH, and less than about 3.0% of stabilizers and lubricants. In a more specific embodiment, containers of the type described above may include approximately 60-70% PVC resin, 15-30% DINCH plasticizer, 5-15% BTHC, approximately 4-10% epoxidized oil and approximately 0.5-3.0% of additional co-stabilizers and lubricants. DINCH is available from, for example, BASF of Ludwigshafen, Germany.

In another embodiment, the plastic composition may include approximately 55%-80%, by weight, PVC and approximately 20%-45% hemolysis-suppressing plasticizer/agent wherein, as a percentage of the overall composition, approximately 3-25% and more preferably 5%-15%, by weight, is a first plasticizer/agent capable of suppressing hemolysis, such as BTHC. In accordance with the present disclosure, the plastic composition may include 55%-80%, by weight, PVC and approximately 20%-45%, by weight, of combined hemolysis-suppressing plasticizer/agent wherein, as a percentage of the overall composition, approximately 5-15% is BTHC, 2-12% epoxidized oil and 15-30% is one or more of ATBC, DINCH or other extractable agents, each of which is effective to suppress hemolysis in red blood cells, with approximately 0.5-3.0% of additional co-stabilizers and lubricants.

The compositions of the present disclosure may also include other additives such as anti-blocking and slip agents. Examples of such anti-blocking and slip agents include derivatives of fatty acid and ethylenediamine. More specifically, the agents may be longer chain fatty acids, containing 12 or longer hydrocarbon chains with or without mono-unsaturated carbon-carbon bonds, based daiamide with ethylendiamine, such as n,n'-ethylene bissteararamide and n,n'-dioleoyl ethylenediamine. Commercially available compounds of the type described above and which may be used in the non-PVC, non-plasticized compositions of the present disclosure include Acrawax and Glycolube, both available from Lonza of Basel, Switzerland. The anti-blocking and/or slip agents may be coated onto the interior surface of the containers or otherwise incorporated therein.

Compositions that include two or more preferably non-phthalate plasticizers or extractable agents are suitable for storing concentrated RBCs with an additive solution. In such applications, any additive solution may be used. In one embodiment, the additive solutions may be any known additive solution, such as SAG-M or Adsol (AS-1) available from Fenwal, Inc., of Lake Zurich, Ill. Alternatively, the additive solution may be the generally hypotonic additive solution described above.

In the embodiments where the container walls (or at least the inner surface(s) 13 of the walls) are made of a material completely free of phthalate, some small trace amounts of phthalate may be present in the container walls as a result of migration from adjoining or adjacent containers, from PVC tubing and/or the surrounding environment generally. In addition, as described above, ports 16 may likewise include PVC and as a result may include some plasticizer (including DEHP). Nonetheless, the presence of some trace amounts of plasticizer attributable to migration from other containers or tubing, or present in the plastic ports 16, is negligible and such containers are referred to herein as "substantially phthalate-free" or "substantially free of phthalate."

Study 1

Whole blood units were collected in CPD anticoagulant in commercially available blood pack units. Within 15 minutes of collection, the units were transferred to non-PVC, non-DEHP polyolefin based containers for pooling. Three units of ABO matched whole blood were pooled together and split back into non-DEHP, non-PVC, polyolefin-based containers. The units were leukofiltered, centrifuged, and processed into plasma and concentrated red cells. Approximately 105 ml of E-Sol 5 was added to each RBC concentrate. The RBC concentrates were then transferred to: (1) a container made of a standard PVC, plasticized with a DEHP (referenced in the Figures as 1.0 DEHP, PVC); (2) a container made of a non-PVC, oxygen semi-permeable material that is a steam sterilizable, multi-component blend that includes a copolymer of polypropylene as its major component with 50% less of the DEHP-plasticizer than the container in subsection (1) above (referenced in the Figures as 0.5 DEHP, non-PVC A), and (3) a container made of a non-PVC plasticizer-free material that is a radiation sterilizable, multi-component blend including primarily ethylene vinyl acetate (referenced in the Figures as 0.0 DEHP, non-PVC B).

Units were stored upright for 42 days at 4° C., with weekly sampling for in vitro parameters. On Day 42 DEHP content in the RBC concentrate was also measured after thorough mixing of each unit.

Study 2

In a further study, whole blood units were collected into CPD anticoagulant in commercially available PVC, plasticizer blood pack units. Within 15 minutes of collection, whole blood units were leukofiltered, centrifuged, and processed into plasma and concentrated RBC component. Approximately 105 ml of E-Sol 5 was added to each red cell concentrate, which was transferred to a container made of a semi gas-permeable, non-PVC material of the type used in the container of subsection (2) in Study 1 described above but substantially free of any plasticizer (referenced in the Figures as 0.0 DEHP, non-PVC A).

Units were stored upright for 42 days at 4° C., with weekly sampling for in vitro parameters. On Day 42 of storage, DEHP content in the RBC concentrate was also measured after thorough mixing of each unit.

Study 3

Whole blood units were collected in CPD anticoagulant in commercially available PVC, plasticizer blood pack units.

Within 15 minutes of collection, the units were transferred to non-PVC, non-DEHP polyolefin based containers for pooling. Two units of ABO matched whole blood were pooled together and split back into the original collection containers. The units were leukofiltered, centrifuged, and processed into plasma and concentrated red cells. Approximately 110 ml of Adsol was added to each RBC concentrate which was then stored in a container identical to the container used to store red cell concentrate in E-Sol, as described above in Study 2 (i.e., referenced in the Figures as 0.0 DEHP, Non PVC A, Adsol and no plasticizer). Paired units were stored upright for 42 days at 4° C., with weekly sampling for in vitro parameters in one unit from each pair (data shown in FIG. 3) and Day 0 and Day 42 sampling only in the other unit from each pair (data not shown). On Day 42 of storage, DEHP content in the RBC concentrate was also measured after thorough mixing of each unit.

Figure 6:
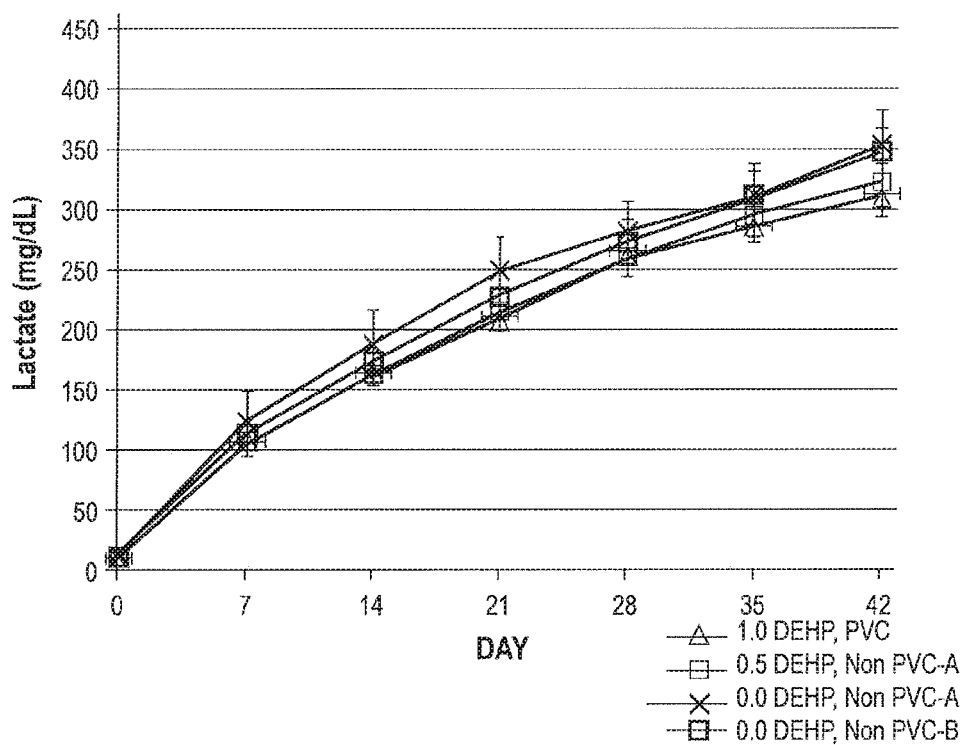
FIG. 6 is a graph showing the levels of lactate over a 42-day storage period of RBCs stored in containers having varying degrees of plasticizer (including no plasticizer)

No major differences were observed in hematocrit, pH, glucose, lactate, phosphate, potassium, 2,3-DPG, and red cell micro particles among the three arms of Study 1 and the single arm of Study 2 described above. As shown in FIG. 3, all E-Sol 5 units passed accepted criteria for hemolysis (below 1.0% and 0.8%, respectively) at Day 42. The Adsol units described in Study 3 had 0.8% hemolysis on average on Day 42. ATP, 2,3-DPG and lactate levels were also comparable in the E-Sol stored units, as also shown in FIGS. 4-6. With reference to Table 1 below, DEHP levels in the non-PVC, non-plasticized containers from Studies 1 and 2 showed negligible DEHP levels of 0.7±0.2 and 2.3+0.8 and 0.9 and +0.2 ppm, respectively in the RBC compositions, thereby indicating that the RBC compositions that are "substantially plasticizer-free" and stored in E-Sol 5 maintained acceptable hemolysis levels.

TABLE 1

| Study | Container/Additive Solution | n | DEHP Content at Day 42 |
|---|---|---|---|
| 1 | 1.0 DEHP, PVC E-Sol 5 | 9 | 34.9 ± 4.7 |
| 1 | 0.5 DEHP, Non PVC-A E-Sol 5 | 8 | 16.7 ± 6.4 |
| 1 | 0.0 DEHP, Non-PVC-B E-Sol 5 | 10 | 0.7 ± 0.2 |
| 2 | 0.0 DEHP, Non PVC-A E-Sol 5 | 9 | 2.3 ± 0.8 |
| 3 | 0.0 DEHP, Non PVC-A Adsol | 6 | 1.8 ± 0.5 |

Studies 4 and 5

Paired, ABO matched WB units in CPD were collected into DEHP-PVC bags and pooled into non-DEHP bags within 15 minutes of collection. Pooled WB units were split into 2 non-DEHP containers and each unit was leukofiltered and processed into plasma and a red cell concentrate (RCC). In Study 4, one RCC was stored in a standard DEHP-PVC bag with 110 mL Adsol (control) and the other RCC in a DINCH-PVC bag with 110 mL Adsol (test). In Study 5, one RCC was stored in a standard DEHP-PVC bag with 110 mL Adsol (control) and the other RCC in a DINCH-PVC bag with 150 mL E-Sol 5 (test). Units were stored upright at 4° C. for 42 days with weekly sampling. On Day 42, DEHP content was quantified for test and control units in Study 1 to ensure there was minimal DEHP exposure during processing and storage of test units. In vitro storage parameter results are summarized in Tables 2 and 3 below.

TABLE 2

| Study 4 | n = 12 pairs | Day 1 | Day 21 | Day 42 |
|---|---|---|---|---|
| ATP ($\mu$mol/g Hb) | Test - DINCH Adsol | 3.7 ± 0.3 | 4.0 ± 0.5* | 2.5 ± 0.4* |
|  | Control - DEHP Adsol | 3.8 ± 0.3 | 4.3 ± 0.6* | 2.7 ± 0.6* |
| Microparticles ($\times 10^3/\mu$L) | Test | 10 ± 4 | 17 ± 5 | 46 ± 12 |
|  | Control | 10 ± 9 | 16 ± 6 | 42 ± 9 |
| Hemolysis (%) | Test | 0.07 ± 0.02 | 0.16 ± 0.05* | 0.39 ± 0.20* |
|  | Control | 0.07 ± 0.01 | 0.12 0.04* | 0.25 ± 0.11* |

TABLE 3

| Study 5 | n = 6 pairs | Day 1 | Day 21 | Day 42 |
|---|---|---|---|---|
| ATP ($\mu$mol/g Hb) | Test - DINCH E-Sol | 4.4 ± 0.3 | 5.0 ± 0.4* | 3.7 ± 0.3* |
|  | Control - DEHP Adsol | 4.4 ± 0.5 | 4.3 ± 0.5* | 3.3 ± 0.4* |
| 2,3 DPG ($\mu$mol/gHb) | Test | 13.6 ± 0.6 | 5.3 ± 3.6* | nt |
|  | Control | 12.9 ± 1.4 | 0.3 ± 0.3* | nt |
| Microparticles ($\times 10^3/\mu$L) | Test† | 4 ± 2 | 10 ± 3* | 25 ± 8* |
|  | Control | 5 ± 3 | 13 ± 2* | 33 ± 7* |
| Hemolysis (%) | Test | 0.07 ± 0.01* | 0.09 ± 0.01* | 0.15 ± 0.02* |
|  | Control | 0.06 ± 0.02* | 0.09 ± 0.01* | 0.16 ± 0.01* |

†normalized for difference in RCC volume
*$p < 0.05$
nt = not tested

Study 6

Figure 7:
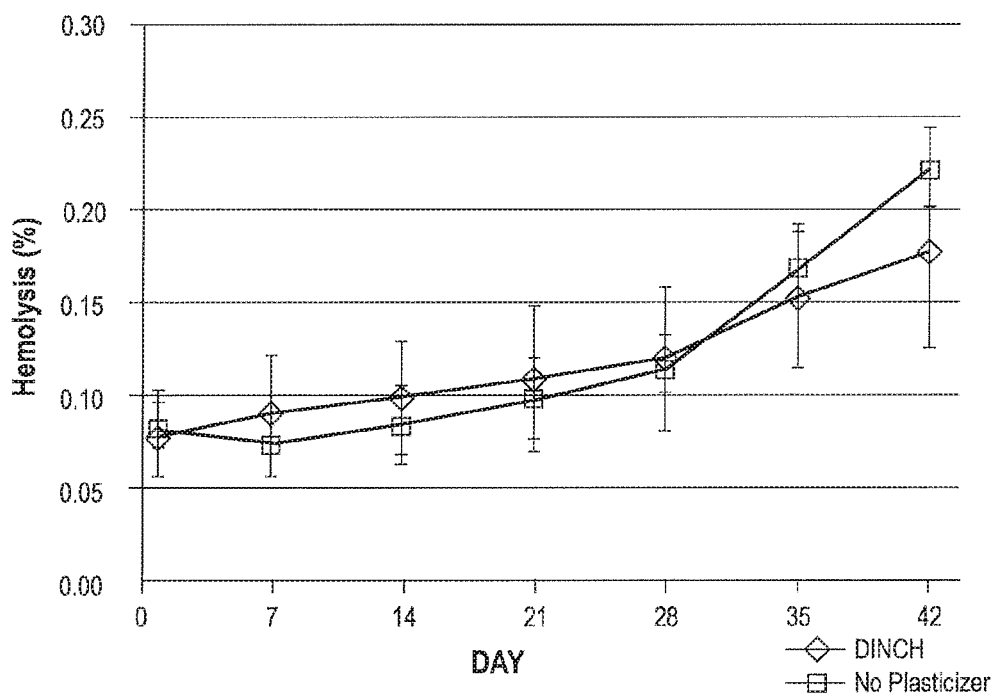
FIG. 7 is a graph showing the levels of hemolysis over a 42-day storage period of RBCs stored in containers made of a non-PVC polyolefin without any plasticizer and including a non-phthalate extractable agent.
Figure 8:
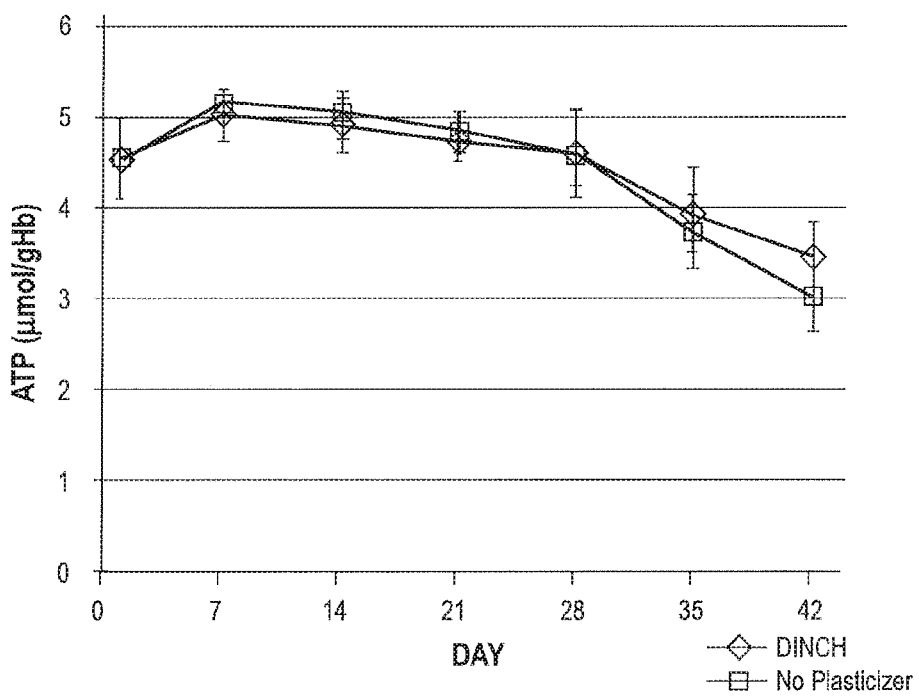
FIG. 8 is a graph showing the levels of ATP over a 42-day storage period of RBCs stored in containers made of non-PVC polyolefin without any plasticizer and including a non-phthalate extractable agent.
Figure 9:
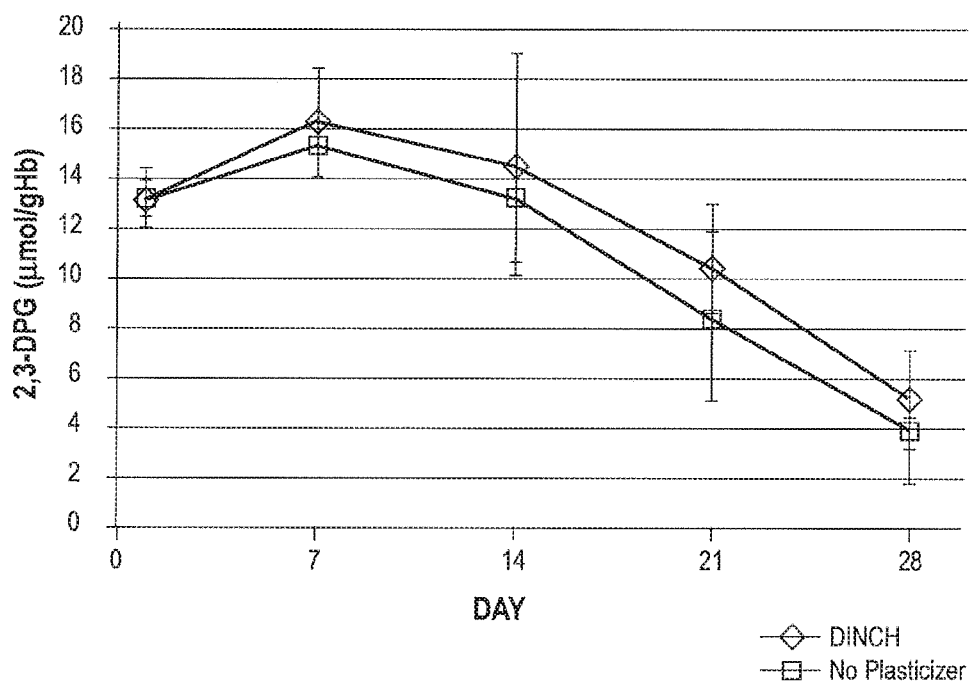
FIG. 9 is a graph showing the levels of 2,3-DPG over a storage period of RBCs stored in containers made of non-PVC polyolefin without any plasticizer and including a non-phthalate extractable agent.

Two (2) ABO matched whole blood units were pooled, split and processed into concentrated RBCs and plasma within four (4) hours of collection. Approximately 105 ml of E-Sol 5 was added to each. The concentrated RBCs in E-Sol 5 were leukofiltered. Each unit of leukofiltered RBCs in E-Sol 5 was stored in a 600 ml plastic container. One container was made of a non-PVC polyolefin without any plasticizer, such as the container referenced as 0.0 DEHP, non-PVC B in Table 1 (and of the type disclosed in U.S. Pat. No. 6,579,583). The other container was made of the same non-PVC polyolefin with DINCH plasticizer coated thereon and gamma irradiated. The RBC compositions described above were stored at 4° C. and samples were drawn every 7 days. The results for 2,3-DPG, % ATP and hemolysis are set forth in FIGS. 7-9.

While the containers, products and compositions disclosed herein have been described in connection with various embodiments, it will be apparent to those skilled in the art that modifications and variations may be made thereto without departing from the spirit and scope of the invention.

The invention claimed is:
1. A red blood cell product comprising:
(a) a container comprising one or more walls defining an interior chamber wherein at least a portion of the wall(s) is made of a polymeric material that is (a) free of phthalate and (b) comprises at least a first extractable agent comprising 1,2-cyclohexane dicarboxylic acid diisononyl ester and a second extractable agent comprising a citrate ester, each of which is effective in suppressing hemolysis in red blood cells, wherein said first extractable agent comprises the majority of said combined first and second extractable agents;

(b) a suspension of red blood cells contained within said chamber, said suspension comprising:
(i) concentrated red blood cells; and
(ii) an additive solution comprising at least a nutrient.

2. The red blood cell product of claim 1 wherein said suspension of red blood cells is suitable for transfusion after about 42 days of storage in said container.

3. The red blood cell product of claim 1 wherein said container further comprises a not readily extractable or marginally extractable plasticizer.

4. The red blood cell product of claim 1 wherein said additive solution comprises sodium chloride, adenine, glucose and mannitol.

5. The red blood cell product of claim 1 wherein said citrate ester is acetyltri-n-butyl citrate.

6. The red blood cell product of claim 1 wherein said citrate ester is n-butyryl-tri-n-hexyl-citrate.

7. The red blood cell product of claim 3 wherein said plasticizer is effective in suppressing hemolysis in red blood cells.

8. The red blood cell product of claim 1 wherein said citrate and 1, 2-cyclohexane dicarboxylic acid diisononyl esters together comprise between 20%-45%, by weight, of said polymeric material.

9. The red blood cell product of claim 1 wherein one of said citrate and 1, 2-cyclohexane dicarboxylic acid diisononyl esters together comprises between approximately 5%-60%, by weight, of the combined weight of said citrate and 1, 2-cyclohexane dicarboxylic acid diisononyl ester and, optionally, additional agents.

10. The red blood cell product of claim 1 wherein said polymeric material comprises polyvinyl chloride, said polyvinyl chloride comprising at least approximately 55%, by weight, of said polymeric material.

11. The red blood cell product of claim 1 wherein said polymeric material comprises approximately 60%-70% polyvinyl chloride, approximately 15%-30% 1, 2-cyclohexane dicarboxylic acid diisononyl ester and approximately 5%-15% citrate ester.

12. The red blood cell product of claim 1 further comprising approximately 4%-10% epoxidized oil.

13. The red blood cell product of claim 12 further comprising approximately 0.5%-3.0% of additional co-stabilizers and lubricants.

14. The red blood cell product of claim 1 wherein said additive comprises:
about 1 mM to 2.2 mM adenine;
about 20 mM to about 110 mM mannitol;
about 2.2 mM to about 90 mM sodium citrate;
about 16 mM to about 30 mM sodium phosphate dibasic; and
about 20 mM to about 140 mM glucose, wherein the pH of the additive solution is at least about 8.0.

15. The red blood cell product of claim 1 wherein said red blood cell product comprises a red blood cell product filtered to remove leukocytes.

* * * * *